(12) United States Patent
Zarembo et al.

(10) Patent No.: US 8,954,167 B2
(45) Date of Patent: Feb. 10, 2015

(54) HELICALLY FORMED COIL FOR A NEURAL CUFF ELECTRODE

(75) Inventors: Paul E. Zarembo, Vadnais Heights, MN (US); Stephen Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1112 days.

(21) Appl. No.: 12/718,462

(22) Filed: Mar. 5, 2010

(65) Prior Publication Data

US 2010/0305674 A1 Dec. 2, 2010

Related U.S. Application Data

(60) Provisional application No. 61/181,072, filed on May 26, 2009.

(51) Int. Cl.
*A61N 1/05* (2006.01)
(52) U.S. Cl.
CPC .................................. *A61N 1/0556* (2013.01)
USPC ....................................................... 607/118
(58) Field of Classification Search
CPC ...... A61N 1/05; A61N 1/0551; A61N 1/0556
USPC ....................................................... 607/118
See application file for complete search history.

(56) References Cited

U.S. PATENT DOCUMENTS

| 4,177,818 | A | 12/1979 | De Pedro |
| 4,573,481 | A | 3/1986 | Bullara |
| 4,590,946 | A | 5/1986 | Loeb |
| 4,590,949 | A | 5/1986 | Pohndorf |
| 4,602,624 | A | 7/1986 | Naples et al. |
| 4,628,942 | A | 12/1986 | Sweeney et al. |
| 4,740,170 | A | 4/1988 | Lee et al. |
| 4,920,979 | A | 5/1990 | Bullara |
| 4,940,065 | A | 7/1990 | Tanagho et al. |
| 4,979,511 | A | 12/1990 | Terry, Jr. |
| 5,031,621 | A | * 7/1991 | Grandjean et al. ............ 600/377 |
| 5,095,905 | A | 3/1992 | Klepinski |

(Continued)

FOREIGN PATENT DOCUMENTS

| JP | 2008526299 A | 7/2008 |
| WO | WO9929366 A1 | 6/1999 |

(Continued)

OTHER PUBLICATIONS

International Search Report and Written Opinion Issued in PCT/US2011/049585, mailed Dec. 19, 2011.

(Continued)

*Primary Examiner* — Christopher D Koharski
*Assistant Examiner* — Frances Oropeza
(74) *Attorney, Agent, or Firm* — Faegre Baker Daniels LLP

(57) ABSTRACT

A lead assembly for an implantable medical device includes a lead body having a proximal end and a distal end. One or more connectors at the proximal end of the lead body are each adapted for connection to a pulse generator. One or more conductive elements are coupled to the one or more connectors at the proximal end and extend through the lead body to the distal end. Each of the one or more conductive elements includes an electrode coil that extends from the distal end of the lead body that is formed into a helix having a diameter greater than a diameter of the electrode coil.

24 Claims, 4 Drawing Sheets

(56) References Cited

U.S. PATENT DOCUMENTS

| | | | |
|---|---|---|---|
| 5,215,089 A | 6/1993 | Baker, Jr. | |
| 5,251,634 A | 10/1993 | Weinberg | |
| 5,259,394 A * | 11/1993 | Bens | 607/127 |
| 5,282,468 A | 2/1994 | Klepinski | |
| 5,324,322 A | 6/1994 | Grill, Jr. et al. | |
| 5,334,438 A | 8/1994 | Saugnac | |
| 5,351,394 A | 10/1994 | Weinberg | |
| 5,358,516 A * | 10/1994 | Myers et al. | 607/116 |
| 5,375,594 A | 12/1994 | Cueva | |
| 5,505,201 A | 4/1996 | Grill, Jr. et al. | |
| 5,531,778 A | 7/1996 | Maschino et al. | |
| 5,674,272 A * | 10/1997 | Bush et al. | 607/122 |
| 5,689,877 A | 11/1997 | Grill, Jr. et al. | |
| 5,755,766 A * | 5/1998 | Chastain et al. | 607/122 |
| 5,782,892 A | 7/1998 | Castle et al. | |
| 5,871,530 A * | 2/1999 | Williams et al. | 607/122 |
| 5,913,876 A | 6/1999 | Taylor et al. | |
| 5,964,702 A | 10/1999 | Grill, Jr. et al. | |
| 6,038,479 A | 3/2000 | Werner et al. | |
| 6,051,017 A | 4/2000 | Loeb et al. | |
| 6,093,197 A | 7/2000 | Bakula et al. | |
| 6,174,329 B1 | 1/2001 | Callol et al. | |
| 6,178,349 B1 | 1/2001 | Kieval | |
| 6,249,708 B1 | 6/2001 | Nelson et al. | |
| 6,292,703 B1 | 9/2001 | Meier et al. | |
| 6,296,659 B1 | 10/2001 | Foerster | |
| 6,308,104 B1 | 10/2001 | Taylor et al. | |
| 6,308,105 B1 | 10/2001 | Duysens et al. | |
| 6,381,499 B1 | 4/2002 | Taylor et al. | |
| 6,423,080 B1 | 7/2002 | Gellman et al. | |
| 6,600,956 B2 | 7/2003 | Maschino et al. | |
| 6,725,096 B2 | 4/2004 | Chinn et al. | |
| 7,047,081 B2 | 5/2006 | Kuzma | |
| 7,054,692 B1 | 5/2006 | Whitehurst et al. | |
| 7,160,298 B2 | 1/2007 | Lawew et al. | |
| 7,212,867 B2 | 5/2007 | Venrooij et al. | |
| 7,502,650 B2 * | 3/2009 | Kieval | 607/45 |
| 7,536,227 B1 | 5/2009 | Poore et al. | |
| 7,561,923 B2 | 7/2009 | Libbus et al. | |
| 7,711,421 B2 | 5/2010 | Shafer et al. | |
| 7,749,273 B2 | 7/2010 | Cauthen, III et al. | |
| 7,807,925 B2 | 10/2010 | Zarembo | |
| 7,831,311 B2 | 11/2010 | Cross, Jr. et al. | |
| 7,891,085 B1 * | 2/2011 | Kuzma et al. | 29/825 |
| 7,925,352 B2 | 4/2011 | Stack et al. | |
| 7,933,662 B2 * | 4/2011 | Marshall et al. | 607/127 |
| 7,957,817 B1 | 6/2011 | Gillespie et al. | |
| 7,974,706 B2 | 7/2011 | Moffitt et al. | |
| 7,996,092 B2 | 8/2011 | Mrva et al. | |
| 8,100,141 B2 | 1/2012 | Slupecki et al. | |
| 8,155,757 B1 | 4/2012 | Neisz et al. | |
| 8,244,372 B1 * | 8/2012 | Zhulati et al. | 607/116 |
| 8,295,948 B2 | 10/2012 | Barker et al. | |
| 8,326,418 B2 * | 12/2012 | Sommer et al. | 607/9 |
| 8,417,343 B2 | 4/2013 | Bolea et al. | |
| 8,483,845 B2 | 7/2013 | Sage | |
| 8,548,593 B2 | 10/2013 | Ternes et al. | |
| 2002/0116042 A1 * | 8/2002 | Boling | 607/122 |
| 2002/0128700 A1 | 9/2002 | Cross, Jr. | |
| 2003/0040785 A1 | 2/2003 | Maschino et al. | |
| 2003/0236558 A1 | 12/2003 | Whitehurst et al. | |
| 2004/0010303 A1 | 1/2004 | Bolea et al. | |
| 2004/0111139 A1 | 6/2004 | McCreery | |
| 2005/0209655 A1 | 9/2005 | Bradley et al. | |
| 2005/0234512 A1 | 10/2005 | Nakao | |
| 2005/0283246 A1 | 12/2005 | Cauthen, III et al. | |
| 2006/0030919 A1 | 2/2006 | Mrva et al. | |
| 2006/0122675 A1 | 6/2006 | Libbus et al. | |
| 2006/0190042 A1 | 8/2006 | Stone et al. | |
| 2006/0259078 A1 | 11/2006 | Libbus | |
| 2007/0071568 A1 | 3/2007 | Dorstewitz | |
| 2007/0083236 A1 | 4/2007 | Sikora et al. | |
| 2007/0100406 A1 | 5/2007 | Kollatschny et al. | |
| 2007/0118177 A1 | 5/2007 | Libbus et al. | |
| 2007/0142871 A1 | 6/2007 | Libbus et al. | |
| 2007/0173914 A1 | 7/2007 | Kollatschny | |
| 2007/0203556 A1 | 8/2007 | Rutten et al. | |
| 2007/0239243 A1 | 10/2007 | Moffitt et al. | |
| 2007/0255320 A1 | 11/2007 | Inman et al. | |
| 2008/0046058 A1 | 2/2008 | Cross et al. | |
| 2008/0051839 A1 | 2/2008 | Libbus et al. | |
| 2008/0058871 A1 | 3/2008 | Libbus et al. | |
| 2008/0058874 A1 | 3/2008 | Westlund et al. | |
| 2008/0058901 A1 | 3/2008 | Ternes et al. | |
| 2008/0086181 A1 | 4/2008 | Amurthur et al. | |
| 2008/0091255 A1 | 4/2008 | Caparso et al. | |
| 2008/0103407 A1 | 5/2008 | Bolea et al. | |
| 2008/0103545 A1 | 5/2008 | Bolea et al. | |
| 2008/0132987 A1 * | 6/2008 | Westlund et al. | 607/122 |
| 2008/0140092 A1 | 6/2008 | Stone et al. | |
| 2008/0172101 A1 | 7/2008 | Bolea et al. | |
| 2008/0177365 A1 | 7/2008 | Bolea et al. | |
| 2008/0177366 A1 | 7/2008 | Bolea et al. | |
| 2008/0183258 A1 | 7/2008 | Inman | |
| 2008/0195188 A1 | 8/2008 | Libbus | |
| 2008/0234780 A1 | 9/2008 | Smith et al. | |
| 2008/0255613 A1 | 10/2008 | Kaiser et al. | |
| 2009/0048641 A1 | 2/2009 | Libbus | |
| 2009/0210042 A1 | 8/2009 | Kowalczewski | |
| 2009/0259260 A1 | 10/2009 | Bentley et al. | |
| 2009/0275997 A1 | 11/2009 | Faltys et al. | |
| 2009/0276024 A1 | 11/2009 | Bonde et al. | |
| 2009/0318961 A1 | 12/2009 | Stone et al. | |
| 2010/0023088 A1 | 1/2010 | Stack et al. | |
| 2010/0036451 A1 | 2/2010 | Hoffer | |
| 2010/0121405 A1 | 5/2010 | Ternes et al. | |
| 2010/0145221 A1 | 6/2010 | Brunnett et al. | |
| 2010/0168831 A1 | 7/2010 | Korivi et al. | |
| 2010/0211131 A1 | 8/2010 | Williams et al. | |
| 2010/0286553 A1 | 11/2010 | Feler et al. | |
| 2010/0312320 A1 | 12/2010 | Faltys et al. | |
| 2010/0331938 A1 | 12/2010 | Sommer et al. | |
| 2011/0004281 A1 | 1/2011 | Jones | |
| 2011/0022142 A1 | 1/2011 | Barker et al. | |
| 2011/0040257 A1 | 2/2011 | Behymer et al. | |
| 2011/0060395 A1 | 3/2011 | Cantlon | |
| 2011/0172682 A1 | 7/2011 | Brady et al. | |
| 2011/0172701 A1 | 7/2011 | Wales et al. | |
| 2012/0022617 A1 | 1/2012 | Tockman et al. | |
| 2012/0035691 A1 | 2/2012 | Tockman et al. | |
| 2012/0065702 A1 | 3/2012 | Arcot-Krishnamurthy et al. | |
| 2012/0221087 A1 * | 8/2012 | Parnis et al. | 607/118 |
| 2013/0005169 A1 | 1/2013 | Soltis et al. | |
| 2013/0013045 A1 | 1/2013 | Soltis | |
| 2013/0172973 A1 | 7/2013 | Tockman et al. | |
| 2013/0253615 A1 | 9/2013 | Arcot-Krishnamurthy et al. | |
| 2013/0253624 A1 | 9/2013 | Tockman et al. | |
| 2014/0094888 A1 | 4/2014 | True et al. | |

FOREIGN PATENT DOCUMENTS

| | | |
|---|---|---|
| WO | WO2004052176 A2 | 6/2004 |
| WO | WO2006093685 A1 | 9/2006 |
| WO | WO2007024164 A1 | 1/2007 |
| WO | WO 2008/088798 | 7/2008 |
| WO | WO2009020639 A1 | 2/2009 |
| WO | WO 2009025817 | 2/2009 |
| WO | WO2009100242 A2 | 8/2009 |
| WO | WO2011053766 A1 | 5/2011 |
| WO | 2013142053 A1 | 9/2013 |

OTHER PUBLICATIONS

International Search Report and Written Opinion Issued in PCT/US2009/063442, mailed Feb. 1, 2010, 11 pages.

International Search Report and Written Opinion Issued in PCT/US2010/026350, mailed Jun. 2, 2010.

International Search Report and Written Opinion Issued in PCT/US2012/044020, mailed Sep. 11, 2012, 9 pages.

International Search Report and Written Opinion issued in PCT/US2012/044028, mailed Oct. 1, 2012, 9 pages.

(56) References Cited

OTHER PUBLICATIONS

International Search Report and Written Opinion issued in PCT/US2011/020699, mailed Jul. 26, 2011, 24 pages.
Partial International Search Report issued in PCT/US2011/020699, mailed Mar. 24, 2011, 6 pages.
International Search Report and Written Opinion issued in PCT/US2013/062560, mailed Dec. 17, 2014, 13 pages.
International Search Report and Written Opinion issued in PCT/US2013/062608, mailed Dec. 17, 2014, 13 pages.
Kirsch, Robert F. et al., "Restoration of Hand and Arm Function by Functional Neuromuscular Stimulation", Period covered: Jun. 1, 2001-Aug. 31, 2006, 71 pages.
International Search Report and Written Opinion issued in PCT/US2013/077949, mailed Jun. 20, 2014, 15 pages.
International Search Report and Written Opinion issued in PCT/US2014/015590, mailed May 28, 2014, 14 pages.
International Search Report and Written Opinion issued in PCT/US2012/071812, mailed Sep. 13, 2013, 12 pages.
International Search Report and Written Opinion issued in PCT/US2013/029306, mailed Jul. 18, 2013, 13 pages.
International Preliminary Examination Report, Chapter II, issued in PCT/US2013/029306, completed Aug. 19, 2014, 16 pages.
Written Opinion of the International Preliminary Examining Authority issued in PCT/US2013/029306, mailed May 8, 2014, 6 pages.

* cited by examiner

HELICALLY FORMED COIL FOR A NEURAL CUFF ELECTRODE

CROSS-REFERENCE TO RELATED APPLICATION

This application claims priority under 35 U.S.C. §119 to U.S. Provisional Application No. 61/181,072, filed on May 26, 2009, entitled "Helically Formed Coil For A Neural Cuff Electrode," which is incorporated herein by reference in its entirety for all purposes.

TECHNICAL FIELD

The present invention relates generally to implantable medical devices. More specifically, the present invention relates to medical device leads including helical neurostimulation electrodes.

BACKGROUND

A significant amount of research has been directed both to the direct and indirect stimulation and sensing of the left and right vagus nerves, the phrenic nerve, the sacral nerve, the cavernous nerve, and portions of the anatomy with baroreceptors (e.g., the carotid artery) to treat a wide variety of medical, psychiatric, and neurological disorders or conditions. For example, stimulation of the vagus nerve has been proposed as a method for treating various heart conditions, including heart failure. The nerves stimulated and/or sensed may be sympathetic or parasympathetic in character.

In a nerve stimulation and sensing system, one or more electrodes are formed on a lead that are electrically connected to an implanted electronic package, such as a pulse generator. Electrical energy is delivered to the electrodes by conductors that extend from the pulse generator at a proximal end of the lead to the electrodes at a distal end of the lead. For direct stimulation of a nerve, the electrodes may be configured to be secured directly to, wrapped around, or laid next to the nerve.

SUMMARY

The present invention relates to a lead assembly for an implantable medical device. The lead assembly includes a lead body having a proximal end and a distal end, and one or more connectors at the proximal end of the lead body that are each adapted for connection to a pulse generator. One or more conductive elements are coupled to the one or more connectors at the proximal end and extend through the lead body to the distal end. Each of the one or more conductive elements includes an electrode coil that extends from the distal end of the lead body that is formed into a helix having a diameter greater than a diameter of the electrode coil.

In another aspect, the present invention relates to a lead assembly for nerve stimulation including a lead body having a proximal end and a distal end. One or more connectors at the proximal end of the lead body are each adapted for connection to a pulse generator, and one or more conductive elements are coupled to the one or more connectors at the proximal end and extend through the lead body to the distal end. Each of the one or more conductive elements includes an electrode coil coupled to a distal end of the conductive element that is formed into a helix having an inner diameter that is sized to couple to a nerve.

In a further aspect, the present invention relates to a nerve stimulation system. The system includes a stimulation device and one or more conductive elements. Each conductive element includes a coil that is electrically coupled to the stimulation device. Each coil includes a distal end that is formed into a helix that is sized to couple to a nerve such that an inner surface of the helix confronts the nerve. The inner surface of each helix is configured to deliver electrical energy to the nerve.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
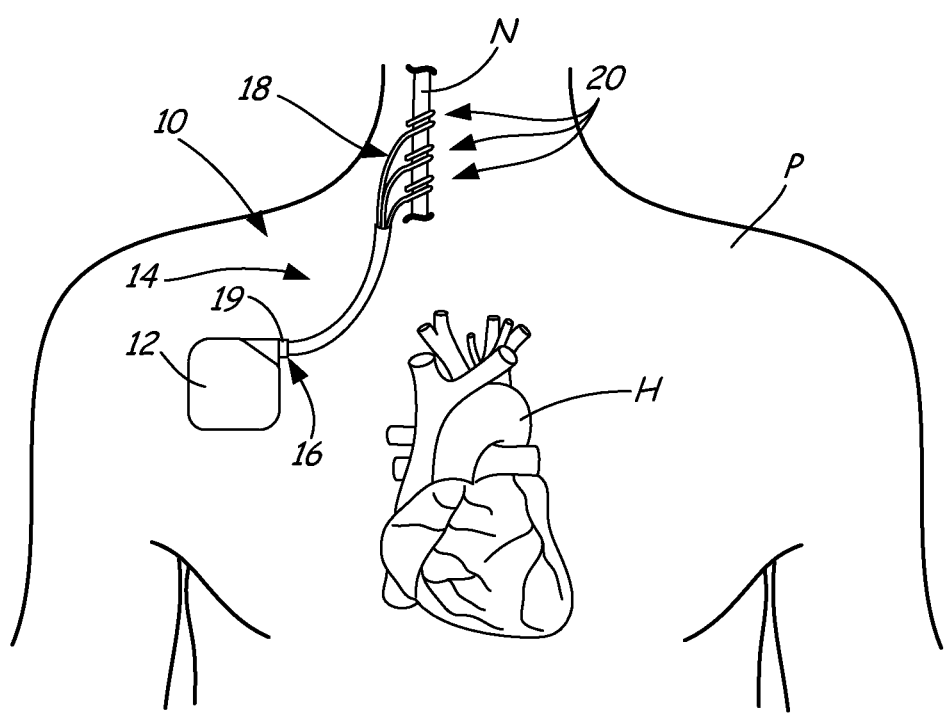
FIG. 1 shows an embodiment of a neurostimulation system according to the present invention and portions of an environment in which the neurostimulation system is used.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows an embodiment of a neurostimulation system 10 according to the present invention implanted in a patient P. The neurostimulation system 10 includes an implantable medical device (IMD) 12 with a lead 14 having a proximal end 16 and a distal end 18. In one embodiment, the IMD 12 includes a pulse generator. The IMD 12 can be implanted subcutaneously within the body, typically at a location such as in a patient's chest or abdomen, although other implantation locations are possible. The proximal end 16 of the lead 14 can be coupled to the IMD 12 via one or more connectors 19. Alternatively, the lead 14 may be formed integrally with the IMD 12. The distal end 18 of the lead 14, in turn, can be implanted at a desired location in the patient's body to stimulate excitable tissue.

The distal end 18 of the lead 14 includes a plurality of electrode cuffs 20. The electrode cuffs 20 are electrically connected to the IMD 12 via one or more conductors (not shown in FIG. 1) extending through the lead 14. As will be described in more detail below, the electrode cuffs 20 are insulated coils or filars that have been formed into a helical shape suitable for coupling to a nerve N, such as a vagus nerve.

During operation, the lead 14 delivers electrical signals between the IMD 12 and the electrode cuffs 20. The electrode cuffs 20 may be separately controlled by IMD 12, such that energy having different magnitude, phase, and/or timing characteristics may be delivered to or from each of the electrode cuffs 20. While the lead 14 shown includes three electrode cuffs 20, any number of electrode cuffs having any arrangement on the lead 14 can alternatively be employed in the system 10. In addition, one or more of the electrode cuffs 20 may alternatively be configured as a strain relief cuff that does not carry electrical signals, but secures the distal end 18 relative to the nerve N to minimize movement of the electrode cuffs 20 relative to the excitable tissue due to voluntary or involuntary movements of the patient. Furthermore, the IMD 12 shown is merely by way of illustration, and the IMD 12 may have any configuration suitable for use in conjunction with the lead 14 and may be implanted in any suitable location in the patient's body.

The electrode cuffs 20 are configured for stimulation or sensing of a nerve or nerve bundle. In the embodiment shown, the distal end 18 is secured to the vagus nerve N. The electrode cuffs 20 may be arranged around the nerve, with the IMD 12 configured to deliver energy to the electrode cuffs 20 to stimulate the nerve. Stimulating the sympathetic and parasympathetic nervous systems can have effects on physiological parameters associated with the heart H, such as heart rate and blood pressure. In addition, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

The vagus nerve N has afferent properties, such that the neural stimulation is transmitted to the central nervous system (CNS). Vagal stimulation simultaneously increases parasympathetic and decreases sympathetic activity, and is believed to prevent further remodeling or predisposition to fatal arrhythmias in post-MI patients, to help restore autonomic balance and increase heart rate variability (HRV), to increase parasympathetic and reduce sympathetic tone in hypertrophic cardiac myopathy (HCM), neurogenic hypertension, and arrhythmia protection, to reduce anginal symptoms, to increase coronary blood flow (CBF), and to prevent development or worsening of congestive heart failure (CHF) following MI. The electrode cuffs 20 may be configured and arranged to stimulate the vagus nerve N to provide any of the physiological responses described. While the electrode cuffs 20 are shown arranged around the right vagus nerve N in FIG. 1, the electrode cuffs 20 can be configured and arranged to stimulate the left vagus nerve N to treat other physiological and psychological conditions, such as epilepsy and depression.

Figure 2:
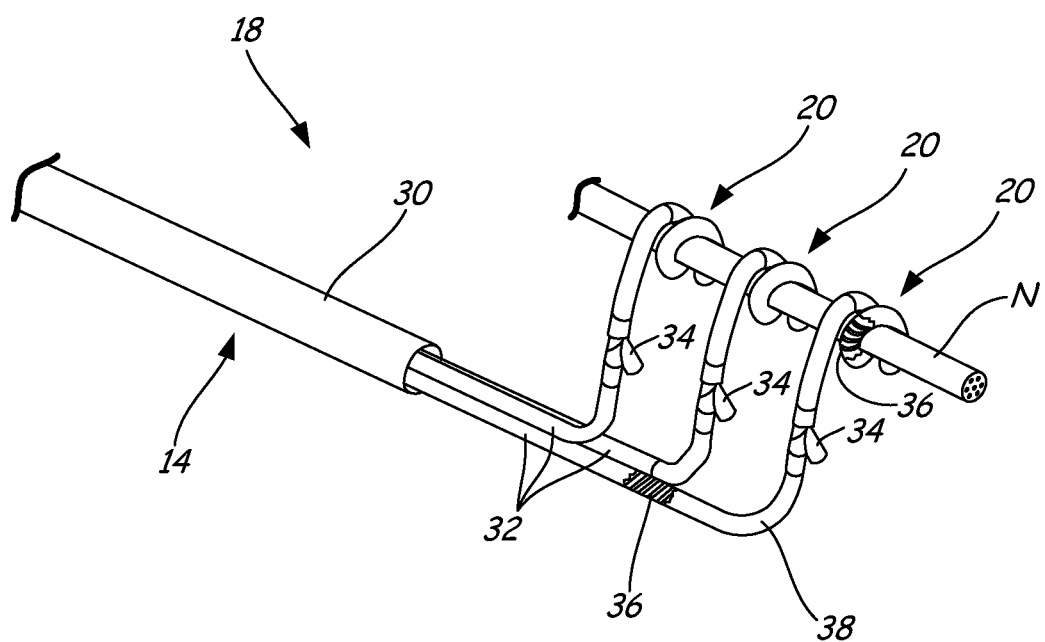
FIG. 2 is a perspective view of a distal end of a neurostimulation lead according to an embodiment of the present invention attached to a nerve bundle.

FIG. 2 is a perspective view of the distal end 18 of the lead 14 according to an embodiment of the present invention. The lead 14 includes a lead body 30 having a plurality of insulated conductors 32 extending therefrom. The insulated conductors 32 each include a lumen access element 34 between the lead body 30 and the helical electrode cuffs 20. The lumen access element 34 will be described in more detail below with regard to FIG. 3. The helical electrode cuffs 20 are shown wrapped around the nerve N such that the inner circumferences of the electrode cuffs 20 (or portions thereof) confront the nerve N.

The lead body 30 extends from the IMD 12 at the proximal end 16 (FIG. 1) to the distal end 18 as shown, and contains the insulated conductors 32. As discussed above, one or more connectors 19 are coupled to the proximal end 16 and are configured to electrically connect the IMD 12 to the insulated conductors 32. In some embodiments, the lead body 30 is made of a flexible, highly durable, fatigue resistant, and biocompatible insulative material. For example, the lead body 30 may be comprised of a polymeric material, such as styrene isoprene butadiene (SIBS), polytetrafluoroethylene (PTFE), polyethylene (PE), polypropylene (PP), fluorinated ethylene propylene (FEP), ethylene-tetrafluoroethylene (ETFE), or another biocompatible polymer.

The insulated conductors 32 each includes an inner conductive coil 36 and an outer insulative layer 38. A conductive coil 36 is illustrated in FIG. 2 via a cutaway portion of the insulative layer 38, but in actual implementation, the insulative layer 38 is substantially continuous along the length of the conductive coil 36. The insulated conductors 32 are shown arranged within the lead body 30 in parallel disposed around the longitudinal axis of the lead body 30. In an alternative embodiment, the conductive coils 36 are arranged co-axially or co-radially within the lead body 30. In such a configuration, the conductive coils 36 are separated and insulated at the distal end 18 to provide multiple electrode cuffs to attach to the nerve N.

In some embodiments, each of the conductive coils 36 includes one or more helically-wound co-radial conductive filars. In the embodiment shown, the conductive coils 36 extend the length of each of the insulated conductors 32 through the lead body 30 and to the distal end of the helical electrode cuffs 20. The conductive coils 36 may be comprised of a biocompatible conductive material, including, but not limited to, MPTa, Pt-clad Ta, Pt-clad MP35N, MP35N, MPAg, and Nitinol.

In an alternative embodiment, the conductive coils 36 are located only in the portion of the insulated conductors 32 on the distal side of the lumen access ports 34. In this latter embodiment, the portion of each insulated conductor 32 on the proximal side of the lumen access ports 34 is electrically coupled to the conductive coil 36, but may have any type of configuration, such as a cable. For example, the cable may have an outer diameter that is less than the inner diameter of the conductive coils 36, allowing the cable to be inserted into the lumen of the conductive coil 36 and secured thereto (e.g., by crimping or laser welding).

The use of conductive coils 36 as the conductor for the electrode cuff 20 has several advantages. For example, coils can provide good compliance to the contours of nerve N, especially if the nerve N swells acutely after implantation. Coils can also provide stability after implantation. In addition, coils provide stretch and lower impact or radial forces to the nerve N compared to conventional foil and wire electrode configurations. Furthermore, coils are robust, have excellent flex fatigue, and do not kink or wrinkle like foil electrodes.

The insulative layer 38 of each insulated conductor 32 may be a tube that is placed over the conductive coil 36, or the insulative layer 38 may be molded over the conductive coil 36. In some embodiments, the insulative layer 38 is made of a flexible, highly durable, fatigue resistant, and bio-compatible insulative material. The insulative layer 38 may be coated with a drug-eluting substance, steroid, or antibiotic. The insulative layer 38 may also be made of a material that allows the electrode cuffs 20 to easily be extracted from the nerve N. For example, the outer insulative layer 38 may be comprised of a polymeric material, such as expanded polytetrafluoroethylene (ePTFE), PTFE, polyurethane, ETFE, ultra-high molecular weight polyethylene (UHMWPE), or another biocompatible polymer. The polymer may be coated or surface treated to make the outer surface more lubricious, hydrophobic, or hydrophylic. The outer insulative layer 38 may alternatively be made of other types of biocompatible material, such as silicone rubber.

When the insulative layer 38 is comprised of an electrically porous material (e.g., ePTFE), the insulative layer 38 allows electrical signals to pass from the conductive coil 36 to the nerve N from portions of the electrode cuffs 20 that confront the nerve N (i.e., the inner circumference of the electrode cuffs 20). In addition, coils that are coated or insulated with ePTFE are easily extractable (e.g., due to infection) because body tissue does not firmly bond to it. In portions of the insulated conductor 32 that do not confront the nerve N, the insulative layer 38 may be electrically sealed to prevent current leakage from the insulated conductor 32. Portions of the insulative layer 38 may be sealed, for example, by applying an electrically non-porous material or adhesive to the portions.

When the insulative layer 38 is comprised of an electrically non-porous material (e.g., silicone rubber), portions of the insulative layer 38 that confront the nerve N are modified to expose the conductive coil 36, thereby making it electrically porous. For example, the inner circumference of the insulated conductor 32 may be laser ablated to allow electrical conductivity between the conductive coil 36 and the nerve N. The portions of the insulative layer 38 that are ablated may be selected to allow for different electrode implantation positions.

When the coils 38 are multifilar, the insulative layer 38 may be configured to allow multiple signals to be delivered by the insulated conductor 32 to the nerve N from different filars. For example, when the insulative layer 38 is comprised of an electrically porous material, the insulative layer 38 may be selectively sealed to make portions of each filar electrically conductive with the nerve N along desired portions of the electrode cuff 20. Similarly, when the insulative layer 38 is comprised of an electrically non-porous material, the insulative layer 38 may be selectively ablated to make portions of each filar electrically conductive with the nerve N along desired portions of the electrode cuff 20. This allows the electrode cuffs 20 to be positioned to better select the nerve or nerves in the nerve bundle to be stimulated.

The helical configuration of the electrode cuffs 20 may be generated in a variety of ways. In one exemplary embodiment, a straight conductive coil 36 is formed, a polymer filament is placed inside and extends from the lumen, and the distal end of the conductive coil 36 is helically wound around a rod or mandrel having a size smaller in diameter and shape similar to the nerve N. A tension force is then applied to the polymer filament in the distal end of the conductive coil 36 that is sufficient to exceed the elastic limit of the conductive coil 36 such that the conductive coil 36 retains the helical shape. This may be accomplished by, for example, securing a weight to the polymer filament in the lumen of the conductive coil 36. In another exemplary embodiment, an insulative elastomeric layer 38 having a distal end pre-molded into a helical shape may be provided with a lumen suitable to receive the conductive coil 36. In this case, a less elastic conductive coil 36 may be used because the insulative layer 38 returns the conductive coil 36 to its helical shape. In a further exemplary embodiment, a Nitinol or other shape memory material may be wound into a helical shape and heat set into the helical shape.

In order to implant and secure the electrode cuffs 20 to the nerve N, the electrode cuffs 20 may be unwound and positioned relative to the nerve N such that, when the electrode cuffs 20 return to their helical shape, they are disposed around and confront the nerve N. One way to accomplish this is to insert a device into the lumen of the conductive coil 36 that extends through the lumen to the distal end of the conductive coil 36 to straighten the electrode cuff 20 for implantation.

Figure 3:
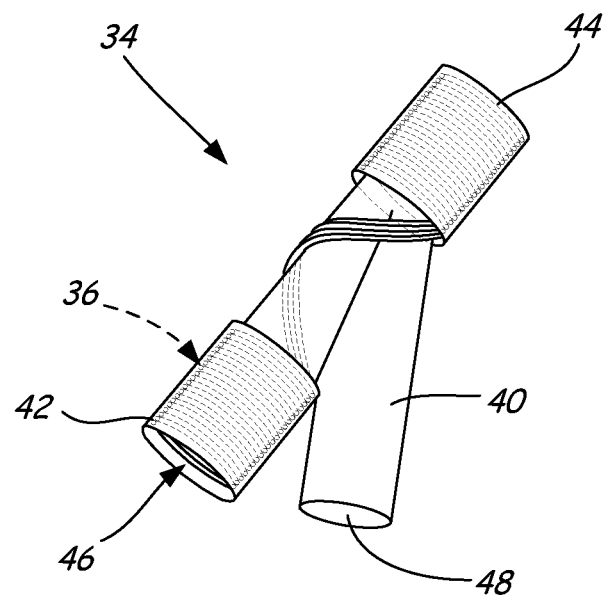
FIG. 3 is a perspective view of a port element for providing access to the lumen of the lead shown in FIG. 2.

For example, FIG. 3 is a perspective view of the lumen access element 34 shown in FIG. 2. The lumen access element 34 includes a lumen access port 40, proximal coil retention element 42, and distal coil retention element 44. The proximal coil retention element 42 and distal coil retention element 44 retain portions of the conductive coil 36 on opposite sides of the lumen access port 40. In the region between coil retention elements 42 and 44, the pitch of the conductive coil 36 is increased to expand the space between adjacent turns in the conductive coil 36. The lumen access port 40 is disposed at an angle relative to the longitudinal axis of the conductive coil 36 and passes between the separated turns of the conductive coil 36 in the region between coil retention elements 42 and 44. The lumen access element 34 allows access to the lumen 46 of the conductive coil 36 via the port opening 48 in the port 40. Consequently, a mandrel-like device may be inserted through the port opening 48 that extends through the port 40 and into the lumen 46 of the conductive coil 36 in the distal coil retention element 44. In some embodiments, the port 40 includes an elastomeric seal plug including an access slit for receiving the device. The length of the device is sufficient to reach the distal end of the electrode cuff 20 through the lumen, thereby straightening the helical portion of the electrode cuff 20. This allows easy placement of the electrode cuffs 20 under nerve N to subsequently wrap around nerve N when the mandrel-like device is removed from the lumen 46.

Figure 4:
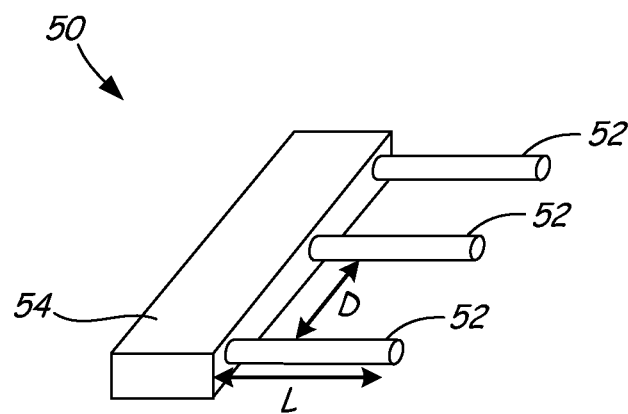
FIG. 4 is a perspective view of a comb-like assembly including mandrels suitable for accessing the lead lumen via the port shown in FIG. 3.

FIG. 4 is a perspective view of a comb-like assembly 50 including mandrels 52 suitable for accessing the lumens of the conductive coils 36 via the port 40 shown in FIG. 3, according to an exemplary embodiment. The mandrels 52 may also be configured for insertion into the lumen of a helical cuff that does not include a conductive coil 36 (e.g., a strain relief cuff). The mandrels 52 are mounted on a handle 54. In some embodiments, the mandrels 52 have a substantially circular cross-section and are comprised of a polymeric material. The mandrels 52 each have a length L that is sufficient to pass through the port 40 of the lumen access element 34 and traverse to the distal end of the electrode cuff 20 via the lumen of the conductive coil 36. Thus, when the mandrels 52 are completely inserted into the lumens 46 of the conductive coils 36, the handle 54 is proximate to the lumen access elements 34. In addition, the mandrels 52 may be spaced apart on the handle 54 by a distance D that provides the desired spacing between adjacent electrode cuffs 20 when secured to the nerve N. In some embodiments, the mandrels 52 are comprised of stainless steel or Nitinol.

In some embodiments, the handle 54 is configured to allow mandrels 52 to be moved and removed to vary the arrangement and number of mandrels 52 on the handle 54. For example, in some situations it may be desirable to manipulate only one electrode cuff 20 at a time, so all but a single mandrels may be removed from the handle 54. Additionally, when a certain spacing of electrode cuffs 20 is desired to stimulate certain nerves in a nerve bundle, the mandrels 52 may be positioned along the handle 54 to provide the desired spacing between the insulated conductors 32.

Prior to implanting the electrode cuffs 20, the mandrels 52 may be inserted into the lumen access ports 40. Consequently, when the electrode cuffs 20 are near the nerve N, the handle 54 may be grasped with a medical instrument or fingers and manipulated to move the electrode cuffs 20 into position. When the electrode cuffs 20 are positioned adjacent to the nerve N, the handle 54 may be manipulated to remove the mandrels 52 from the lumens 46 of the conductive coils 36, thereby allowing the electrode cuffs to return to their helical shape and wrap around the nerve N.

It should be noted that, while the lumen access element 34 shown and described above with regard to FIG. 3 has a particular configuration, any assembly that provides access to the lumens of the conductive coils 36 is contemplated by the present invention. For example, access to the lumen 46 may be provided at the proximal end 16 of the lead 14, such that the mandrel traverses substantially the entire length of the lead 14 to straighten the electrode cuffs 20. If the lead 14 includes multiple conductive coils 36 that each terminate in an electrode coil 20, access to each lumen 46 may be provided at the proximal end 16. In addition, while the assembly 50 of FIG. 4 is shown having a comb-like configuration, any suitable arrangement of mandrels may be used to straighten the electrode cuffs 20 when securing the electrode cuffs 20 to the nerve N.

Figure 5A:
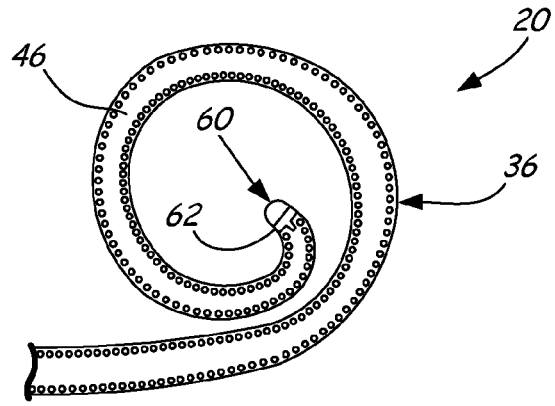
FIGS. 5A-5C illustrate steps for coupling the lead electrode cuffs of the neurostimulation lead shown in FIG. 2 to a nerve bundle.
Figure 5B:
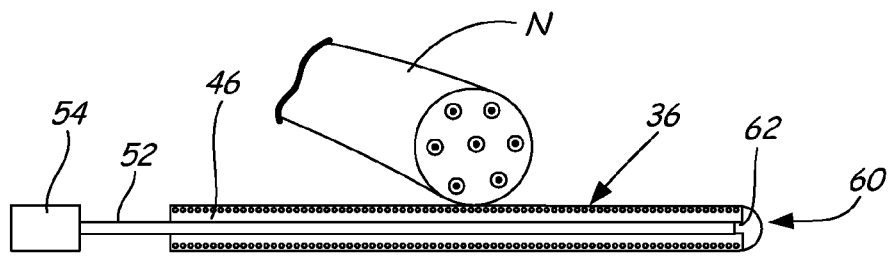
Figure 5C:
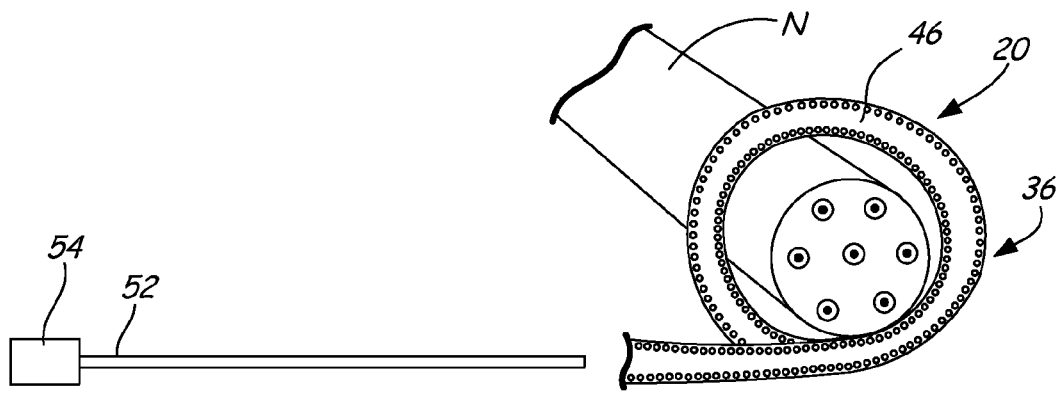

To illustrate the process of implanting the lead 14, FIGS. 5A-5C illustrate steps for coupling the electrode cuffs 20 to the nerve N. FIG. 5A is a cross-sectional view of an electrode cuff 20 in its normal helical configuration. The electrode cuff 20 includes a conductive coil 36 that extends to the distal end 60 of the electrode cuff 20. A lumen 46 extends axially through the conductive coil 36. In some embodiments, a lumen cap 62 is included provided at the distal end of the conductive coil 36 to provide an end cap to the lumen 46.

FIG. 5B is a cross-sectional view of the electrode cuff 20 with a mandrel 52 extending through the lumen 46 of the conductive coil 36. As discussed above, the mandrel 52 may be inserted prior to implantation of the electrode cuff 20. The mandrel 52 is inserted into the lumen 46 via, for example, lumen access port 40, and a force is applied to the handle 54 to move the mandrel 52 through the electrode cuff 20. As the mandrel 52 traverses the lumen 46, the electrode cuff 20 unwinds into a substantially straight configuration. The mandrel 52 is forced through the lumen 46 until the mandrel 52 confronts the lumen cap 62, at which point the electrode cuff 20 is completely unwound. The handle 54 is then manipulated to position the unwound electrode cuff 20 adjacent to the nerve N at a location that allows the electrode cuff 20 to stimulate the desired portion of the nerve N. In one exemplary embodiment, the mandrel 52 has a diameter in the range of about 0.1 mm to about 0.3 mm, and the conductive coil 36 has an inner diameter in the range of about 0.2 mm to about 0.5 mm.

FIG. 5C is a cross-sectional view of the electrode cuff 20 after the mandrel 52 has been removed from the lumen 46. To remove the mandrel 52 from the lumen 46, the handle 54 is pulled away from the lumen access port 40. As the mandrel 52 exits the lumen, the distal end 60 winds around the nerve N. The mandrel 52 is removed until the electrode cuff 20 is wrapped around the nerve N. The inner diameter of the electrode cuff 20 is sized such that the inner circumference of the electrode cuff 20 confronts the outer surface of the nerve N. In one exemplary embodiment, the inner diameter of the electrode cuff 20 is in the range of about 1 mm to about 5 mm.

While the neural cuffs 20 have been described as being provided on the distal end 18 of a lead 14, in other embodiments, the neural cuffs 20 as described may be provided in other system configurations suitable for delivering signals to a nerve N. For example, the neural cuffs 20 may be provided as part of a transdermal microstimulator system in which the neural cuffs 20 are connected to a device that is implanted beneath the skin. The device may include power and control circuitry, for example. An external control device, which may be wearable, may be employed to inductively couple with the device to power and control the implanted system. One example microstimulator system into which the neural cuffs 20 may be integrated is described in U.S. Pat. No. 6,051,017, entitled "Implantable Microstimulator and Systems Employing the Same," which is incorporated by reference in its entirety.

In summary, the present invention relates to a lead assembly for an implantable medical device. The lead assembly includes a lead body having a proximal end and a distal end, and one or more connectors at the proximal end of the lead body that are each adapted for connection to a pulse generator. One or more conductive elements are coupled to the one or more connectors at the proximal end and extend through the lead body to the distal end. Each of the one or more conductive elements includes an electrode coil that extends from the distal end of the lead body that is formed into a helix having a diameter greater than a diameter of the electrode coil. The helices of the lead are easily implantable, for example using a mandrel-like device as described herein. In addition, the helices are easily extracted from the nerve, for example in case of infection.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A lead assembly for an implantable medical device, the lead assembly comprising:
   a lead body having a proximal end and a distal end;
   one or more connectors at the proximal end of the lead body that are each adapted for connection to a pulse generator; and
   one or more conductive elements coupled to the one or more connectors at the proximal end and extending through the lead body to the distal end, wherein each of the one or more conductive elements comprises an electrode coil that extends from the distal end of the lead body, and wherein the electrode coil is formed into a helix at the distal end having a diameter greater than a diameter of the electrode coil.

2. The lead assembly of claim 1, wherein each electrode coil includes a lumen extending through the electrode coil to the distal end of the conductive element.

3. The lead assembly of claim 2, wherein the lumen is accessible with a mandrel employable to unwind the helix during implantation.

4. The lead assembly of claim 3, wherein the mandrel is provided on a comb-like structure including a plurality of mandrels each employable to unwind the helix of one of the one or more electrode coils.

5. The lead assembly of claim 1, wherein each electrode coil is at least partially surrounded by a biocompatible insulator.

6. The lead assembly of claim 5, wherein the biocompatible insulator is selected from the group consisting of expanded polytetrafluoroethylene (ePTFE), PTFE, polyurethane, ethylene tetrafluoroethylene (ETFE), ultra-high molecular weight polyethylene (UHMWPE), and silicone rubber.

7. The lead assembly of claim 1, wherein each electrode coil is comprised of a biocompatible material selected from the group consisting of MPTa, Pt-clad Ta, Pt-clad MP35N, MP35N, MPAg, and Nitinol.

8. A lead assembly for nerve stimulation, the lead assembly comprising:
a lead body having a proximal end and a distal end;
one or more connectors at the proximal end of the lead body that are each adapted for connection to a pulse generator; and
one or more conductive elements coupled to the one or more connectors at the proximal end and extending through the lead body to the distal end, wherein each of the one or more conductive elements includes an electrode coil coupled to a distal end of the conductive element, and wherein the electrode coil is formed into a helix having an inner diameter that is sized to couple to a nerve.

9. The lead assembly of claim 8, wherein each electrode coil includes a lumen extending through the electrode coil.

10. The lead assembly of claim 9, wherein the lumen is accessible with a mandrel employable to straighten the helix during implantation.

11. The lead assembly of claim 8, wherein each electrode coil is at least partially surrounded by a biocompatible insulator.

12. The lead assembly of claim 11, wherein the biocompatible insulator is electrically porous, and wherein portions of each helix that do not confront the nerve are electrically sealed.

13. The lead assembly of claim 11, wherein the biocompatible insulator is not electrically porous, and wherein portions of each helix that confront the nerve are ablated.

14. The lead assembly of claim 11, wherein the biocompatible insulator is selected from the group consisting of expanded polytetrafluoroethylene (ePTFE), PTFE, polyurethane, ethylene tetrafluoroethylene (ETFE), ultra-high molecular weight polyethylene (UHMWPE), and silicone rubber.

15. The lead assembly of claim 8, wherein each electrode coil is comprised of a biocompatible material selected from the group consisting of MPTa, Pt-clad Ta, Pt-clad MP35N, MP35N, MPAg, and Nitinol.

16. A neurostimulation system comprising:
a stimulation device; and
one or more conductive elements each comprising a coil that is electrically coupled to the stimulation device, each coil including a distal end that is formed into a helix that is sized to couple to a nerve such that an inner surface of the helix confronts the nerve, wherein the inner surface of each helix is configured to deliver electrical energy to the nerve.

17. The neurostimulation system of claim 16, wherein the stimulation device comprises a pulse generator, and wherein the neurostimulation system further comprises:
a lead body having a proximal end and a distal end, wherein the one or more conductive elements extend through the lead body; and
one or more connectors at the proximal end of the lead body that are connectable to the pulse generator, wherein the one or more conductive elements are connected to the one or more connectors at the proximal end.

18. The neurostimulation system of claim 16, wherein the stimulation device comprises an implantable microstimulator.

19. The neurostimulation system of claim 16, wherein each coil includes a lumen extending through the helix.

20. The neurostimulation system of claim 19, wherein the lumen is accessible with a mandrel employable to straighten the helix during implantation.

21. The neurostimulation system of claim 16, wherein each helix is at least partially surrounded by a biocompatible insulator.

22. The neurostimulation system of claim 21, wherein the biocompatible insulator is electrically porous, and wherein portions of each helix that do not confront the nerve are electrically sealed.

23. The neurostimulation system of claim 21, wherein the biocompatible insulator is not electrically porous, and wherein portions of each helix that confront the nerve are ablated.

24. The neurostimulation system of claim 21, wherein the biocompatible insulator is selected from the group consisting of expanded polytetrafluoroethylene (ePTFE), PTFE, polyurethane, ethylene tetrafluoroethylene (ETFE), ultra-high molecular weight polyethylene (UHMWPE), and silicone rubber.

* * * * *